United States Patent
Shaw (10) Patent No.: US 9,445,794 B2
(45) Date of Patent: Sep. 20, 2016

(54) CATHETER FOR USE WITH AN ENDOSCOPE

(71) Applicant: Boston Scientific Scimed, Inc., Maple Grove, MN (US)

(72) Inventor: William J. Shaw, Cambridge, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 14/560,150

(22) Filed: Dec. 4, 2014

(65) Prior Publication Data

US 2015/0087901 A1 Mar. 26, 2015

Related U.S. Application Data (63) Continuation of application No. 11/405,225, filed on Apr. 17, 2006, now Pat. No. 8,926,499.

(51) Int. Cl.

| | | |
|---|---|---|
| A61B 1/00 | (2006.01) | |
| A61B 1/04 | (2006.01) | |
| A61M 31/00 | (2006.01) | |
| A61M 37/00 | (2006.01) | |
| A61B 17/00 | (2006.01) | |
| A61B 1/018 | (2006.01) | |
| A61M 25/00 | (2006.01) | |

(52) U.S. Cl.
CPC ..... *A61B 17/00234* (2013.01); *A61B 1/00098* (2013.01); *A61B 1/00133* (2013.01); *A61B 1/018* (2013.01); *A61B 2017/0034* (2013.01); *A61B 2017/00407* (2013.01); *A61M 2025/006* (2013.01)

(58) Field of Classification Search
USPC ........ 600/104, 106, 107, 114–115, 127, 129, 600/153, 170, 171; 604/103.04, 164.01, 604/164.12, 165.01
See application file for complete search history.

(56) References Cited

U.S. PATENT DOCUMENTS

| | | |
|---|---|---|
| 1,644,919 A | 10/1927 | Hayes |
| 2,919,697 A | 1/1960 | Kim |
| 4,166,468 A | 9/1979 | Haynie |
| 4,285,341 A | 8/1981 | Pollack |
| 4,445,892 A | 5/1984 | Hussein et al. |
| 4,606,347 A | 8/1986 | Fogarty et al. |
| 4,730,616 A | 3/1988 | Frisbie et al. |
| 4,771,777 A | 9/1988 | Horzewski et al. |

(Continued)

FOREIGN PATENT DOCUMENTS

| | | | |
|---|---|---|---|
| EP | 0380227 A2 | 8/1990 | |
| EP | 0416734 A1 | 3/1991 | |
| JP | 2004159771 A | * 6/2004 | ............... A61B 1/00 |

OTHER PUBLICATIONS

Brugge, William R. et al., "Medical Progress: Pancreatic and Biliary Endoscopy," New England Journal of Medicine, vol. 341, No. 24, Dec. 9, 1999, pp. 1808-1816.

(Continued)

*Primary Examiner* — Ryan Henderson
(74) *Attorney, Agent, or Firm* — Bookoff McAndrews, PLLC (57) ABSTRACT

Endoscopes, medical devices for use with endoscopes, and methods for making and using endoscopes. An example medical device for use with an endoscope is a catheter having one or more ridges formed on an outer surface thereof. The ridges may interact, for example, with the elevator of an endoscope.

19 Claims, 10 Drawing Sheets

(56) References Cited

U.S. PATENT DOCUMENTS

| | | | |
|---|---|---|---|
| 4,798,193 A | 1/1989 | Giesy et al. |
| 4,820,271 A | 4/1989 | Deutsch |
| 4,820,349 A | 4/1989 | Saab |
| 4,827,941 A | 5/1989 | Taylor et al. |
| 4,832,028 A | 5/1989 | Patel |
| 4,838,268 A | 6/1989 | Keith et al. |
| 4,844,092 A | 7/1989 | Rydell et al. |
| 4,846,174 A | 7/1989 | Willard et al. |
| 4,881,547 A | 11/1989 | Danforth |
| 4,917,102 A | 4/1990 | Miller et al. |
| 4,932,959 A | 6/1990 | Horzewski et al. |
| 4,944,740 A | 7/1990 | Buchbinder et al. |
| 4,976,689 A | 12/1990 | Buchbinder et al. |
| 5,040,548 A | 8/1991 | Yock |
| 5,669,878 A | 9/1997 | Dickinson et al. |
| 5,785,689 A | 7/1998 | De Toledo et al. |
| 5,921,971 A | 7/1999 | Agro et al. |
| 5,938,585 A | 8/1999 | Donofrio |
| 5,989,230 A | 11/1999 | Frassica |
| 6,007,522 A | 12/1999 | Agro et al. |
| 6,096,009 A | 8/2000 | Windheuser et al. |
| 6,102,887 A | 8/2000 | Altman |
| 6,152,910 A | 11/2000 | Agro et al. |
| 6,228,039 B1 | 5/2001 | Binmoeller |
| 6,251,084 B1 | 6/2001 | Coelho |
| 6,270,465 B1 | 8/2001 | Keith et al. |
| 6,277,065 B1 | 8/2001 | Donofrio |
| 6,299,628 B1 | 10/2001 | Harrison et al. |
| 6,312,404 B1 | 11/2001 | Agro et al. |
| 6,346,093 B1 | 2/2002 | Allman et al. |
| 6,379,338 B1 | 4/2002 | Garvin |
| 6,443,912 B1 | 9/2002 | Mazzola et al. |
| 6,520,951 B1 | 2/2003 | Carrillo, Jr. et al. |
| 6,582,401 B1 | 6/2003 | Windheuser et al. |
| 6,606,515 B1 | 8/2003 | Windheuser et al. |
| 6,663,597 B1 | 12/2003 | Windheuser et al. |
| 6,746,442 B2 | 6/2004 | Agro et al. |
| 6,827,683 B2 | 12/2004 | Otawara |
| 6,869,416 B2 | 3/2005 | Windheuser et al. |
| 6,879,854 B2 | 4/2005 | Windheuser et al. |
| 6,997,908 B2 | 2/2006 | Carrillo, Jr. et al. |
| 7,060,052 B2 | 6/2006 | Windheuser et al. |
| 7,063,659 B2 | 6/2006 | Goto et al. |
| 7,076,285 B2 | 7/2006 | Windheuser et al. |
| 7,232,434 B2 | 6/2007 | Suyama et al. |
| 8,109,872 B2 | 2/2012 | Kennedy et al. |
| 2002/0087100 A1 | 7/2002 | Onuki et al. |
| 2004/0186461 A1 | 9/2004 | DiMatteo |
| 2005/0143770 A1 | 6/2005 | Carter et al. |
| 2006/0047246 A1 | 3/2006 | Anders |
| 2007/0208221 A1 | 9/2007 | Kennedy et al. |

OTHER PUBLICATIONS

Internet Article: http://www.olympusamerica.com/msg_section/msg_product_print.asp?product=1144, "Olympus V-Scope(TM)—TJF—160 VF," printed Aug. 1, 2005, 2 sheets.

Internet Article: http://www.olympusamerica.com/msg_section/vsys/vsys_faq.asp "Frequently Asked Questions," printed Aug. 1, 2005, 2 sheets.

* cited by examiner

CATHETER FOR USE WITH AN ENDOSCOPE

This application is a continuation of U.S. patent application Ser. No. 11/405,225, filed on Apr. 17, 2006, which is incorporated herein by reference in its entirety.

FIELD

The present invention pertains to endoscopes and medical devices for use with endoscopes. More particularly, the present invention pertains to endoscopic catheters with one or more ridges or protrusions formed thereon.

BACKGROUND

A wide variety of endoscopes, medical devices for use with endoscopes, and endoscopic procedures have been developed. Of the known endoscopes, medical devices for use with endoscopes, and endoscopic procedures, each has certain advantages and disadvantages. There is an ongoing need to provide alternative endoscopes as well as methods for making and using endoscopes.

SUMMARY

The invention provides design, material, and manufacturing method alternatives for endoscopes, medical devices for use with endoscopes, and for methods for making and using medical devices and/or endoscopes. An example medical device for use with an endoscope is a catheter having one or more ridges or protrusions formed thereon at desired locations along the catheter shaft. The ridges or protrusions may interact, for example, with the elevator of an endoscope. Some additional details regarding these and other embodiments are described in more detail below.

The above summary is not intended to describe each disclosed embodiment or every implementation of the present disclosure. The Figures and Detailed Description which follow more particularly exemplify these embodiments.

BRIEF DESCRIPTION OF THE DRAWINGS

The disclosure may be more completely understood in consideration of the following detailed description of various embodiments of the disclosure in connection with the accompanying drawings, in which.

DETAILED DESCRIPTION

The following detailed description should be read with reference to the drawings in which similar elements in different drawings are numbered the same. The drawings, which are not necessarily to scale, depict illustrative embodiments and are not intended to limit the scope of the invention.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

A vast number of endoscopic devices exist that have a wide variety of applications. In at least some applications, the position of the endoscopic device and/or the position of a particular medical device disposed in the endoscopic device is important. This is because it may be challenging to precisely navigate the endoscope or endoscopic instruments through the anatomy of a patient. For example, when endoscopes are used for biliary applications, it may be difficult to advance an endoscopic medical device through the papilla of Vater and toward the bile duct as it exits the working channel of the endoscope. Moreover, once a device is successfully advanced through the papilla of Vater, subtle movement of the device can result in the device being withdrawn back out from the papilla of Vater, necessitating another round of skilled maneuvering, in order to proceed with the intervention.

When dealing with the position of a guidewire, a number of proximal "wire locks" have been developed that are disposed near the proximal handle of the endoscope. There is an ongoing need for improved devices for securing the position of guidewires within the working channel of an endoscope.

For at least some of the same reasons that are desirable to control the position of a guidewire, controlling the position of a catheter disposed in the working channel of an endoscope may be also desirable. In addition, it may be desirable to hold, advance, and retract a catheter in a controlled manner for a number of different interventions.

Figure 1:
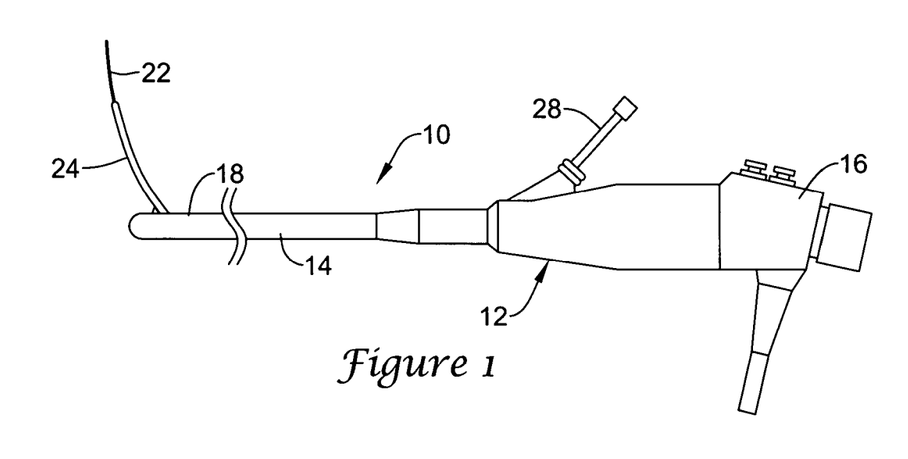
FIG. 1 is a schematic plan view of an illustrative endoscopic instrument assembly.

FIG. 1 is an example endoscopic instrument assembly 10 that addresses at least some of these needs as well as provides a number of additional desirable features. Assembly 10 includes an endoscope 12 having a shaft portion 14 and a handle portion 16. Shaft portion 14 includes a distal end region 18 and a distal port 20 (best seen in FIG. 2) where one or more medical devices (e.g., a guidewire 22 and/or a catheter 24) are disposed within a working channel 26 (best seen in FIG. 2) formed in shaft portion 14 with medical devices capable of extending distally from distal port 20. An elevator 36 can be disposed adjacent port 20 that when actuated alters the angle at which guidewire 22 and/or catheter 24 exits port 20. Handle portion 16 includes one or more openings or a control region 28 where instruments (e.g., endoscopic instruments, guidewires, catheters, and the like) can gain access to working channel 26 and be extended through shaft portion 14 and out from port 20. Control region 28 may also include a control wire (not shown) for controlling elevator 36.

Figure 2:
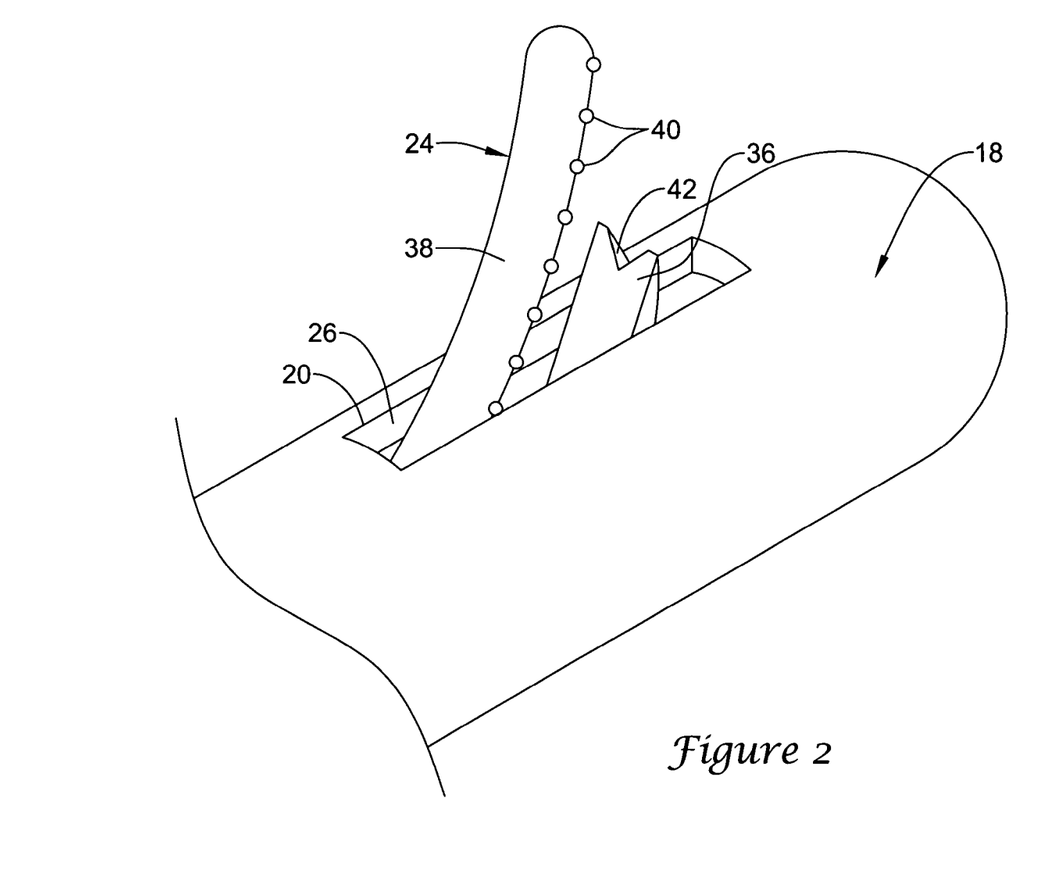
FIG. 2 is a perspective view of an illustrative medical device disposed in the working channel of an illustrative endoscope.
Figure 3:
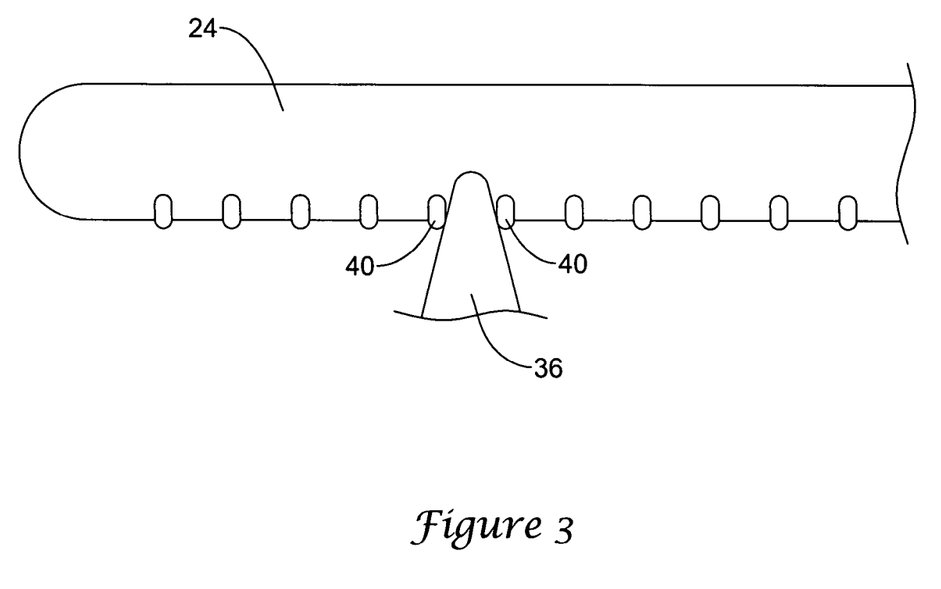
FIG. 3 is a side elevation view of the illustrative medical device shown FIG. 2 engaged with an elevator.

For the reasons stated above, it may be desirable for assembly 10 to include one or more features or a plurality of features that allow a user to hold, advance, and retract a catheter disposed in working channel 26. Turning now to FIG. 2, it can be seen that catheter 24 includes one or more protrusions, ribs or ridges 40 disposed at the distal end region 38 of catheter 24. Ridges 40 project outward from catheter 24 and are spaced so that elevator 36 can fit between adjacent ridges 40 when elevator 36 is actuated as depicted in FIG. 3. Because of the arrangement of ridges 40, actuating elevator 36 so that it is disposed between adjacent ridges 40 holds the position of catheter 24 within working channel 26. The ridges or ribs 40 can be any useful form that can engage the actuating elevator, as desired.

Elevator 36 can also include a number of features that contribute to the control of catheter 24. For example, elevator 36 includes a notch 42 formed therein that is designed to improve the fit between catheter 24 and elevator 36. More particularly, notch 42 is shaped so that elevator 36 can more securely contact and hold catheter 24 in place. In some embodiments, notch 42 also allows elevator 36 to be actuated against guidewire 22 so that guidewire 22 can be secured between elevator 38 and the wall of shaft portion 18. Thus in some embodiments, elevator 38 is designed with the ability to secure the position of catheter 24 and guidewire 22.

The shape or configuration of notch 42 (i.e., the shape of elevator 36 adjacent notch 42) can vary depending on the application. For example, in some embodiments, notch 42 is "V-shaped" or "U-shaped". These shapes are desirable because they allow notch 42 to substantially conform to the outer surface of a medical device such as catheter 24. This may improve the ability for elevator 36 to securely hold the position of catheter 24.

Figure 2A:
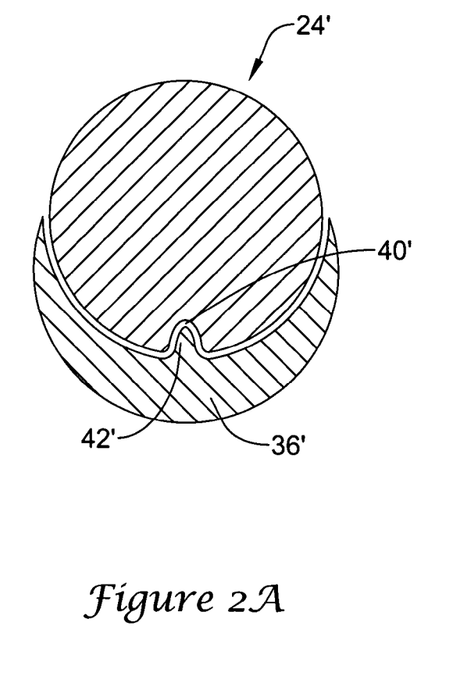
FIG. 2A is a cross-sectional view of another illustrative medical device disposed adjacent an illustrative elevator.

In addition, the arrangement of ridges 40 and notch 42 can be reversed. For example, in some embodiments the "ridge" may be formed on the elevator, whereas the "notch" may be disposed on the medical device as depicted in FIG. 2A. Here it can be seen that medical device 24' includes a channel or notch 40'. Elevator 36' may be used with device 24', and elevator 36' includes a ridge 42' that is configured to mate with notch 40. This concept of altering the arrangement of ridges and notches can be utilized for essentially any embodiment disclosed herein.

Figure 4:
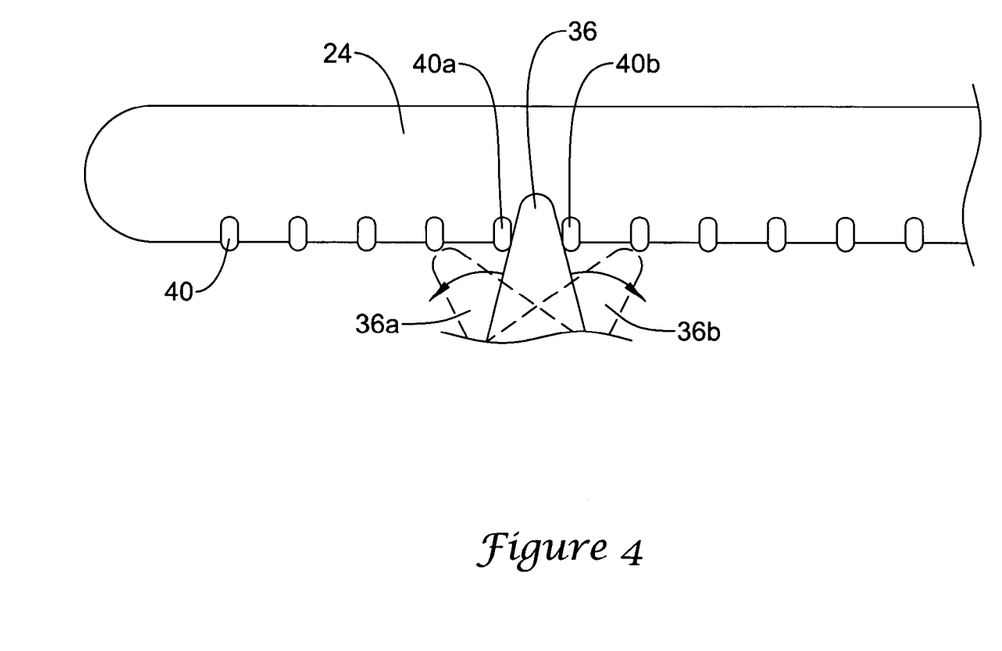
FIG. 4 is a side elevation view of the movement of the elevator relative to the illustrative medical device.

Another feature of assembly 10 is illustrated in FIG. 4. Here it can be seen that in addition to being able to hold the position of catheter 24, elevator 36 and ridges 40 on catheter 24 can function together like a ratchet so that catheter 24 can be moved in a step-wise manner in opposing directions such as, for example, either in the proximal or the distal direction. For example, allowing elevator 36 to move downward (e.g., by releasing tension on the elevator control wire) to position 36a applies a small amount of force onto ridge 40a, thereby advancing catheter 24 in the distal direction. Similarly, actuating elevator 36 (e.g., by adding tension to the elevator control wire) applies force onto ridge 40b, thereby advancing catheter 24 in the proximal direction. Once catheter 24 is moved in either direction and once there is enough clearance over ridges 40, elevator 36 can "ratchet" back into a position between two adjacent ridges 40. This once again secures the position of catheter 24. If desired, additional ratchet steps can be performed to move catheter 24 in either the proximal or distal direction.

In some embodiments, catheter 24 may be an endoscopic guide catheter. However, catheter 24 need not necessarily be a guide catheter as catheter 24 can be any suitable catheter or related medical device for use with endoscopes. The use of catheter 24 may be similar to the use of typical endoscopic catheters. For example, catheter 24 may be advanced through the working channel of an endoscope to a location adjacent an area of interest. Catheter 24 may then be used for its intended purpose. For example, if catheter 24 is a guide catheter then another diagnostic or therapeutic medical device may be advanced over or through (i.e., through a lumen defined therein) catheter 24.

Ridges 40 may be formed on catheter 24 in a number of different ways. For example, ridges 40 may be extruded onto catheter 24. Alternatively, ridges 40 may be adhesively bonded, welded, mechanically attached, brazed, or otherwise coupled to catheter 24 in any other suitable way. In some embodiments, ridges 40 may be formed on an adhesive-backed strip of material that can be adhered to catheter 24. This embodiment may be desirable, because it allows ridges 40 to be added to essentially any catheter suitable for use with an endoscope.

In some embodiments, ridges 40 may be made from a polymer material that is attached to catheter 24 using any suitable method (such as those listed above). Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane, polypropylene (PP), polyvinylchloride (PVC), polyether-ester (for example, ARNITEL® available from DSM Engineering Plastics), ether or ester based copolymers (for example, butylene/poly (alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof, polymer/metal composites, and the like.

Alternatively, ridges 40 may be made from a metal, metal alloy, metal-polymer composite, or the like. Examples of suitable metals and metal alloys include stainless steel, such as 304V, 304L, and 316LV stainless steel; mild steel; nickel-titanium alloy such as linear-elastic or super-elastic nitinol, nickel-chromium alloy, nickel-chromium-iron alloy, cobalt alloy, tungsten or tungsten alloys, MP35-N (having a com-position of about 35% Ni, 35% Co, 20% Cr, 9.75% Mo, a maximum 1% Fe, a maximum 1% Ti, a maximum 0.25% C, a maximum 0.15% Mn, and a maximum 0.15% Si), hastelloy, monel 400, inconel 825, or the like; other Co—Cr alloys; platinum enriched stainless steel; or other suitable material.

In some embodiments, ridges 40 may also be made from, doped with, or otherwise include a radiopaque material. Radiopaque materials are understood to be materials capable of producing a relatively bright image on a fluoroscopy screen or another imaging technique during a medical procedure. This relatively bright image aids the user of catheter 24 in determining its location. Some examples of radiopaque materials can include, but are not limited to, gold, platinum, molybdenum, palladium, tantalum, tungsten or tungsten alloy, plastic material loaded with a radiopaque filler, and the like.

Figure 4A:
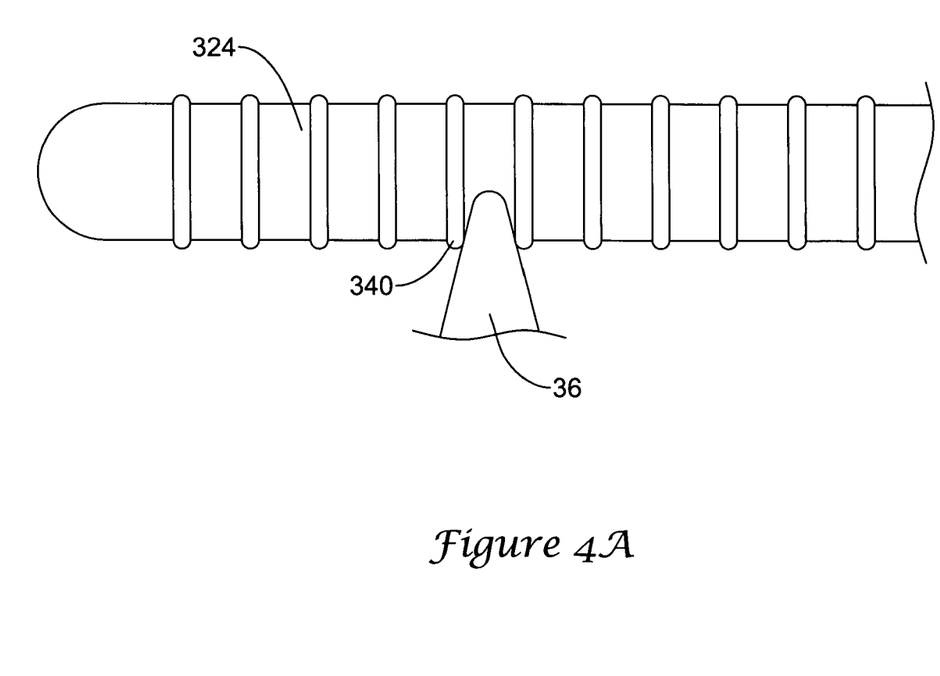
FIG. 4A is a side elevation view of another illustrative medical device.
Figure 4B:
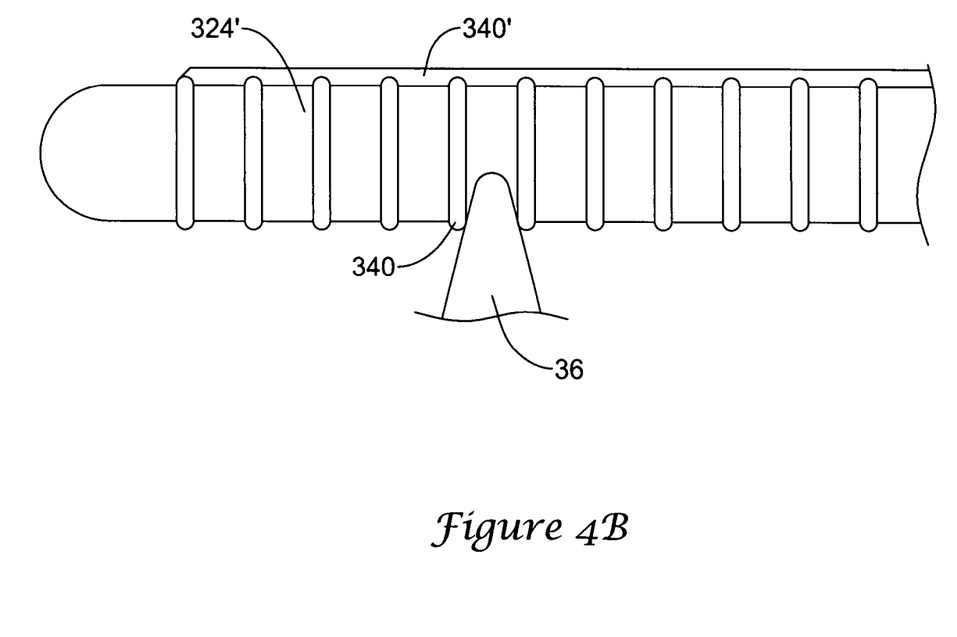
FIG. 4B is a side elevation view of another illustrative medical device.

Another example medical device 324 is shown in FIG. 4A. Here it can be seen that ridges 340 define ring-like structures that extend around device 324. Ridges 340 function much like ridges 40 and, consequently, can interact with elevator 36 in a similar manner. In some embodiments, a longitudinal ridge 340', in addition to ridges 340, may be disposed on device 324' as shown in FIG. 4B. Longitudinal ridge 340' may extend along the longitudinal axis of device 324', and it may be configured to fit within elevator 36 in a manner that allows longitudinal movement of device 324. Rotation of device 324' so that longitudinal ridge 340' is "disengaged" from elevator 36 allows ridges 340 to substantially secure the longitudinal position of device 324' in essentially the same way that ridges 40 secure the position of device 24.

Figure 5:
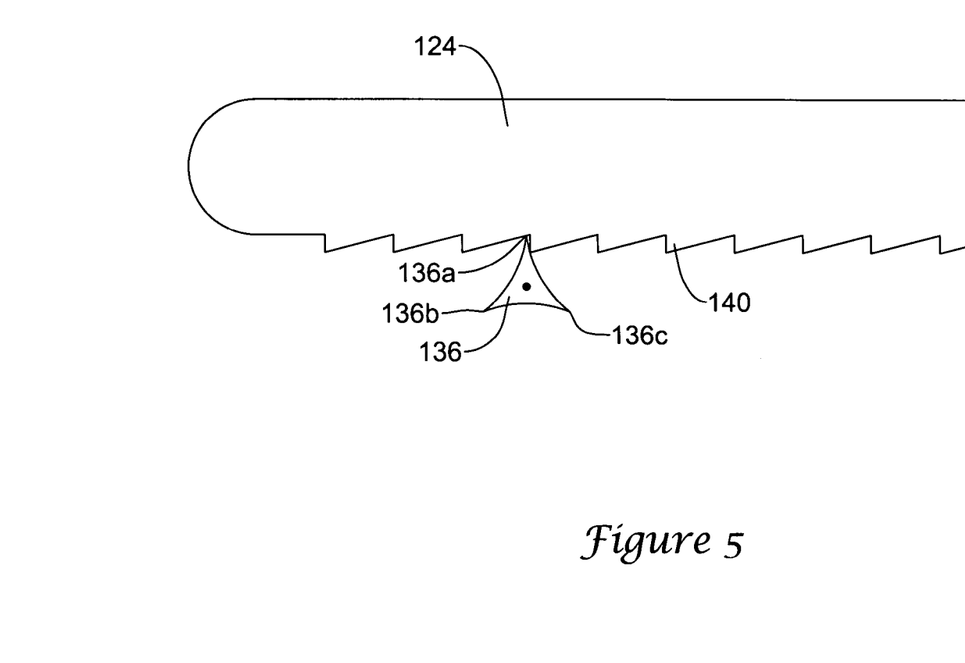
FIG. 5 is a side elevation view of another illustrative medical device.

FIG. 5 illustrates another example catheter 124 that is similar in form and function to catheter 24 except that ridges 140 on catheter 124 form a plurality of teeth or teeth-like projections. Teeth 140 are arranged or spaced so that elevator 136 can be disposed between adjacent "fangs". In addition, elevator 136 and teeth 140 can be ratcheted so that catheter 140 can be distally advanced or proximally retracted in addition to being held in position. The steps and mechanism for ratcheting teeth 140 is analogous to how ridges 40 are ratcheted.

FIG. 5 also depicts that elevator 136 may have a different shape and that elevator 136 may be rotatable. These features may be desirable, for example, because they may allow the orientation and/or position of elevator 136 to be utilized to shift the position of device 124. For example, elevator 136 is shown to have a shape that resembles a triangle. The "points" 136a/136b/136c of the triangle can press against teeth 140 so that as elevator 136 is rotated in a counter-clockwise direction, one or more of points 136a/136b/136c can engage teeth 140 in a manner that distally advances device 124. Conversely, clockwise rotation of elevator 136 may be utilized for retracting device 124. Other shapes are contemplated such as star-shaped, polygonal-shaped, etc., that can be similarly used to achieve movement of device 124. Rotation of elevator 136 may be controlled using conventional means such as with the use of a control wire.

Figure 6:
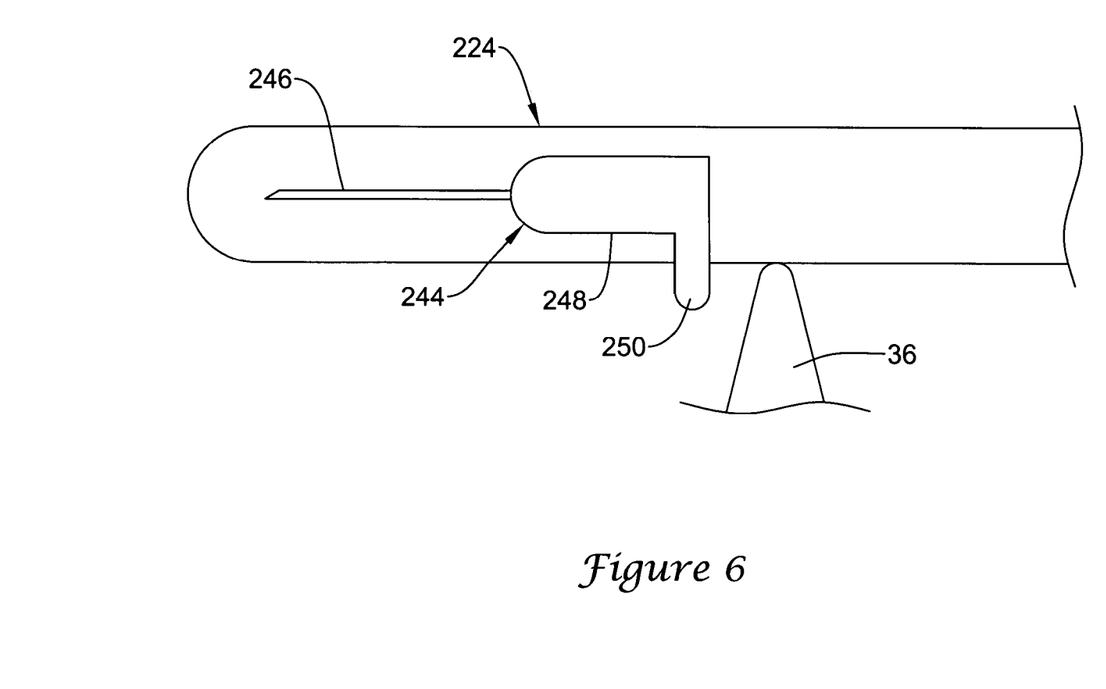
FIG. 6 is a side elevation view of another illustrative medical device engaged with an elevator.
Figure 7:
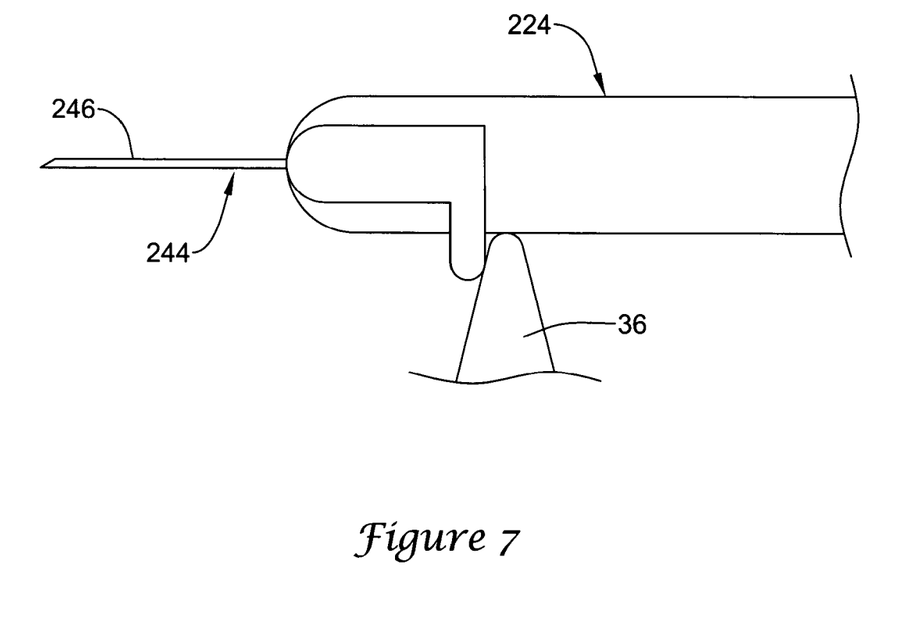
FIG. 7 is a side elevation view of the medical device shown in FIG. 6 where the elevator is activated so as to activate the medical device.

FIG. 6 illustrates another example catheter 224 that can be used with an endoscope. Catheter 224 includes a sliding needle apparatus 244 having a needle 246 attached to a needle housing 248. A trigger 250 is also attached to housing 248. Sliding needle apparatus 244 is configured to interact with elevator 36 so that needle 246 can be slid out from catheter 224. In some embodiments, elevator 36 is actuated so that elevator 36 contacts catheter 224. Once in this position, catheter 224 can be proximally retracted so that trigger 250 engages elevator 36. Catheter 224 can then be further retracted so that force is applied to trigger 250, causing trigger 250 to slide within catheter 224 until needle 246 emerges from the distal end of catheter 224 as shown in FIG. 7.

In other embodiments, elevator 36 can press against and hold the position of catheter 224. Then, elevator 36 can be lowered (e.g., by releasing tension from the elevator control wire), thereby exerting a distal force on trigger 250. The force on trigger 250 slides needle 246 distally out from catheter 224.

It can be appreciated that the interaction of elevator 36 with the various ridges can be utilized to carry out a number of additional functions. For example, in some embodiments, needle 246 may extend out from catheter 224 and trigger 250 may act like a syringe plunger to administer fluids, therapeutic or diagnostic agents, or any other suitable material from needle 246. Alternatively, trigger 250 may control a cutting device such as a clevis or clamp coupled to catheter 224. Moreover, trigger 250 may control a visualization apparatus such as a camera. For example, trigger 250 may slide the camera out from catheter 224 or otherwise turn on or adjust the camera.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A medical instrument assembly comprising:
    a shaft including:
        a distal end region having a port,
        a working channel in communication with the port, and
        an elevator positioned at the port, the elevator including a recess; and
    a medical device configured for positioning in the working channel, and capable of extending distally from the port, the medical device including:
        at least one first protrusion projecting outwardly from a surface of the medical device, the at least one first protrusion extending circumferentially along the surface, and
        a second protrusion projecting outwardly from the surface, the second protrusion extending longitudinally along the surface, wherein the second protrusion intersects the at least one first protrusion such that the second protrusion extends at least from a proximal end of the at least one first protrusion to a distal end of the at least one first protrusion,
    wherein the medical device is movable relative to the elevator between a first configuration, with the recess engaging a surface of the medical device beside the at least one first protrusion, and a second configuration, with the recess engaging the second protrusion.

2. The medical instrument assembly of claim 1, wherein the second protrusion extends further from the surface than the at least one first protrusion.

3. The medical instrument assembly of claim 1, wherein the second protrusion extends parallel to a longitudinal axis of the medical device.

4. The medical instrument assembly of claim 3, wherein the at least one first protrusion extends perpendicular to the longitudinal axis.

5. The medical instrument assembly of claim 1, wherein the at least one first protrusion includes a plurality of first protrusions axially spaced apart from each other, and each of the first protrusions extends around a circumference of the medical device.

6. The medical instrument assembly of claim 5, wherein the second protrusion intersects the plurality of first protrusions.

7. The medical instrument assembly of claim 1, wherein the at least one first protrusion is annular.

8. The medical instrument assembly of claim 1, wherein the second protrusion is linear.

9. A medical instrument assembly comprising:
a shaft including:
a distal end region having a port,
a working channel in communication with the port, and
an elevator positioned at the port, the elevator including a notch; and
a medical device configured for positioning in the working channel, and capable of extending distally from the port, the medical device including:
a plurality of first protrusions on a first side of the medical device, and
a second protrusion on only a second side of the medical device, the second protrusion extending at an angle relative to the first protrusions, and the second protrusion intersecting at least one of the first protrusions,
wherein the medical device is configured to move relative to the elevator between a first configuration, with the notch engaging a surface of the medical device beside at least one of the first protrusions, and a second configuration, with the notch engaging the second protrusion.

10. The medical instrument assembly of claim 9, wherein the medical device is rotatable relative to the elevator to position the elevator and the medical device in the first and second configurations.

11. The medical instrument assembly of claim 9, wherein the first side is opposite the second side.

12. The medical instrument assembly of claim 9, wherein in the first configuration, engagement between at least one of the first protrusions and the elevator holds the medical device in position relative to the shaft.

13. The medical instrument assembly of claim 9, wherein in the second configuration, engagement between the second protrusion and the notch positions the elevator out of engagement with the first protrusions, facilitating longitudinal sliding of the medical device relative to the shaft.

14. The medical instrument assembly of claim 9, wherein the second protrusion extends longitudinally along a surface of the medical device, and the second protrusion intersects the first protrusions.

15. The medical instrument assembly of claim 9, wherein the second protrusion has a greater height than the first protrusions.

16. An endoscopic instrument assembly comprising:
an endoscope including a shaft, the shaft having:
a distal end region with a port,
a working channel in communication with the port, and
an elevator positioned at the port, the elevator including a notch; and
a catheter configured for introduction into the working channel and extension distally from the port, the catheter including:
a plurality of first protrusions on a first side of the catheter, wherein the first protrusions are spaced apart in a proximal-distal direction along the first side of the catheter, and
a second protrusion on a second side of the catheter, the second protrusion intersecting the first protrusions,
wherein the catheter is configured to move relative to the elevator between a first configuration, with the notch engaging a surface of the catheter between adjacent first protrusions, and a second configuration, with the notch engaging the second protrusion.

17. The endoscopic instrument assembly of claim 16, wherein in the first configuration, engagement between adjacent first protrusions and the elevator holds the catheter in position relative to the working channel.

18. The endoscopic instrument assembly of claim 16, wherein in the second configuration, engagement between the second protrusion and the notch positions the elevator out of engagement with first protrusions, facilitating longitudinal sliding of the catheter along the working channel.

19. The endoscopic instrument assembly of claim 16, wherein the second protrusion extends across the first protrusions.

* * * * *